United States Patent
Lehmann et al.

(10) Patent No.: US 7,554,135 B2
(45) Date of Patent: Jun. 30, 2009

(54) DEVICE FOR DETECTING A GAS OR GAS MIXTURE

(75) Inventors: Mirko Lehmann, Freiburg (DE); Heinz-Peter Frerichs, St. Peter (DE); Christoph Wilbertz, Gundelfingen (DE)

(73) Assignee: Micronas GmbH, Freiburg i.Br. (DE)

( * ) Notice: Subject to any disclaimer, the term of this patent is extended or adjusted under 35 U.S.C. 154(b) by 411 days.

(21) Appl. No.: 10/592,848

(22) PCT Filed: Mar. 4, 2005

(86) PCT No.: PCT/EP2005/002283

§ 371 (c)(1),
(2), (4) Date: Sep. 14, 2006

(87) PCT Pub. No.: WO2005/093399

PCT Pub. Date: Oct. 6, 2005

(65) Prior Publication Data

US 2008/0237654 A1    Oct. 2, 2008

(30) Foreign Application Priority Data

Mar. 18, 2004   (DE) ........................ 10 2004 013 678

(51) Int. Cl.
    H01L 23/58   (2006.01)
(52) U.S. Cl. ........................ 257/253; 257/414; 73/31.06
(58) Field of Classification Search ................. 257/253, 257/414; 73/31.06; 438/49
    See application file for complete search history.

(56) References Cited

U.S. PATENT DOCUMENTS

| 4,650,561 A | 3/1987 | Robins et al. |
| 4,730,479 A | 3/1988 | Pyke et al. |
| 5,279,795 A * | 1/1994 | Hughes et al. ................. 422/98 |
| 2002/0131898 A1 | 9/2002 | Fleischer et al. |
| 2002/0170824 A1 | 11/2002 | Frerichs |

FOREIGN PATENT DOCUMENTS

| DE | 4333875 C2 | 4/1995 |
| DE | 100 36 178 A1 | 2/2002 |
| DE | 101 61 214 B4 | 7/2003 |
| WO | 95/29072 | 11/1995 |
| WO | 03/050526 A | 6/2003 |

OTHER PUBLICATIONS

Eisele I et al.: "Work function based field effect devices for gas sensing" Optoelectronic and Microelectronic Materials and Devices. 2000. Proc. Dec. 6, 2000, pp. 285-291, XP010596262.

(Continued)

*Primary Examiner*—Mark Prenty
(74) *Attorney, Agent, or Firm*—The Webb Law firm

(57) ABSTRACT

A device for detecting a gas or gas mixture having at least one first gas sensor designed as an SGFET and at least—one second, additional gas sensor designed as a Lundström-FET. The gas sensors are connected to a processing device designed to analyze the measurement signals from both types of gas sensors in order to detect the gas or gas mixture.

18 Claims, 4 Drawing Sheets

OTHER PUBLICATIONS

T. Doll, I. Isele: "Gas detection with work function sensors" Proc. SPIE Conference on Chemical Microsensors and Applications, vol. 3539, Nov. 1998, pp. 96-105, XP002329891.

P. Bergveld, J. Hendrikse, W. Olthuis: "Theory and application of the material work function for chemical sensors based on the field effect principle" Meas. Sci. Technol., vol. 9, 1998, pp. 1801-1808, XP002329892.

Lundström I. et al.: "A Hydrogen-sensitive MOS field-effect transistor", Appl. Phys. Lett. 26 (2), Jan. 15, 1975, XP002086960.

I. Eisele, T. Doll, M. Burgmair: "Low power gas detection with FET sensors", Sensors and Actuators B, 2001, vol. 78, S. 19-25.

M Fleischer, B. Ostrick, R. Pohle, E. Simon, H. Meixner, C. Bilger, F. Daeche: "Low-Power gas sensors based on work-function measurement in low-cost hybrid flip-chip technology", Sensors and Actuators B, 2001, vol. 80, S. 169-173.

PCT International Preliminary Report, Jun. 2005.

PCT Written Opinion of International Searching Authority (Translation), Nov. 2006.

PCT International Search Report (German), Jun. 2005.

PCT International Search Report (English Translation), Jun. 2005.

German Office Action, Feb. 2005.

* cited by examiner

DEVICE FOR DETECTING A GAS OR GAS MIXTURE

BACKGROUND OF THE INVENTION

1. Field of the Invention

The invention concerns a device consisting of at least one Lundström-FET gas sensor, for detecting a gas or a gas mixture.

2. Description of Related Art

Such a device for detecting hydrogen gas is well known from DE 43 33 875 C2. As a gas sensor, it consists of a transistor called the Lundström Field Effect transistor. The Lundström-FET has a gas-sensitive coating which is capacitatively coupled between an electrical insulating coating and the channel domain of the FET. The Lundström-FET works on the basis of the principle that hydrogen atoms separated or adsorbed from the environment become polarized and bring about a change in the threshold voltage of the FET when they reach the boundary between the gas layer and the insulating layer. The disadvantage here, however, is that in order to reach the insulating layer, the hydrogen atom must be diffused through the gas-sensitive layer. For that reason, the Lundström-FET has a relatively slow response time. Admittedly, the response time can be reduced by heating the Lundström-FET, but this requires a not insignificant use of energy. Moreover, the Lundström-FET has a certain sensitivity to other gases besides hydrogen.

A hydrogen detection device is well known from DE 43 33 875 C2, which is a gas-sensor based on the principle of the Suspended Gate Field Effect Transistors (SGFET), with a gas-sensitive coating that is capacitatively coupled across an air gap to a channel domain placed between a Source- and a Drain domain. The gas-sensitive coating reacts when it comes into contact with hydrogen gas, by changing its output, which induces a voltage on the surface of the coating, which sends the current across the channel domain between the Source- and the Drain domain. The gas-sensitive coating, however, is also sensitive to other gases besides hydrogen. In environments in which such other gases might be found, the detection of hydrogen gas can become very imprecise. This is the case, for example, for detecting leaks in the hydrogen fuel lines for motor vehicles using hydrogen as a source of fuel.

Because hydrogen gas is highly explosive when it comes into contact with atmospheric oxygen, any leak must be detected as quickly as possible, in order to either block the delivery of hydrogen and/or to warn the user of the motor vehicle, before a critical concentration of hydrogen gas in the surrounding air is exceeded. However, false alarms which might occur because of the cross-sensitivity of the gas-sensor to other gases should be avoided in all circumstances, since such false alarms might lead to cutting off the supply of hydrogen fuel, and the stalling of the motor vehicle.

The objective therefore is to make to make a device of the above-cited kind, which will make it possible to detect a gas with greater precision and reliability. The other objective is to create a device of the above-cited kind, which will make it possible to detect in a simple fashion, a gas mixture consisting of at least of two gases.

SUMMARY OF THE INVENTION

The first cited objective is solved by means of building the device with at least one gas sensor consisting of a Lundström-FET, and another gas sensor consisting of an SGFET; where at least one Lundström-FET and one SGFET are connected to a processing device, which is configured in such a way that it can analyze the sensor signals of both kinds of gas-sensors for the detection of gases or gas mixtures.

The knowledge underlying the invention is that the Lundström-FET and the SGFET have distinct characteristics for the detection of gases, and that through the apparently unnecessary combination of these two kinds of gas-sensors and the analysis of the different sensor signals, these gas sensors can detect gases with a significantly greater precision than could be done by a device outfitted with only one kind of gas-sensor. In particular, the device according to the invention makes it possible to have a much lower cross-sensitivity towards gases other than the one to be detected, since the SGFET and the Lundström-FET have different sensitivities, so that through the comparison of the sensor signals of the two kinds of gas-sensors, when leak-proofing tests are being done in a motor vehicle in actual testing, it is possible to detect in a given case, to what degree the sensor signal was caused by the motor vehicle's fuel gas, and/or at least one other gas.

In a second functional embodiment of the invention, the Lundström-FET has a first Drain and a first Source located upon the substrate of a semiconductor chip, between which a first channel domain is to be found, which is provided with a first gas-sensitive coating, which reacts by changing its output when there is a change in the concentration of the gas to be detected, and is capacitatively coupled across a dielectric coating to the first channel domain, where the SGFET is located upon the substrate next to the Lundström-FET of a second Drain and a second Source, between which a second channel domain is to be found, which has a Suspended Gate with a second gas-sensitive coating, which reacts by changing its output when there is a change in the concentration of the gas to be detected, and/or of a gas different from the former, to which the Lundström-FET has a cross-sensitivity, and is capacitatively coupled across an air gap to a second channel domain. For this application, a processing device can be configured in such a way that it analyzes the sensor signals of both kinds of gas sensors, in order to compensate for cross-sensitivity. The dielectric coating preferably consists of $SiO_2$, $Si_3N_4$, $Al_2O_3$, or a mixed oxide of these materials.

A preferred embodiment of the invention would have at least a second Drain, a second Source, a second channel domain and a Gate-Electrode of at least one SGFET, of at least one Lundström-FET and, as the case may be, a processing device integrated on the same semi-conductor chip. On the one hand, this makes possible a compact and economical device, while on the other hand, the close-packed spatial arrangement of the gas-sensors ensures that the gas coming into contact with the individual gas sensors will have the same composition. Moreover, integrating the gas sensors on the semiconductor chip ensures that the gas sensors will have the same temperature. This device thus makes it possible to measure and detect gas with greater precision and reliability. Preferably the first gas-sensitive coating would consist of palladium and/or a palladium alloy, and the second gas-sensitive coating of palladium and/or platinum and/or at least an alloy containing one of these metals. These materials make it possible to attain particularly high detection sensitivities for hydrogen gas. Ammonia ($NH_3$) also, and/or nitrogen dioxide ($NO_2$) can be measured with the device in accordance with the invention.

In one embodiment of the invention, the Suspended Gate is lengthened on one side until it reaches the Lundström-FET, and preferably covers it completely. The device can then be produced simply and economically with the state-of-the-art materials for semiconductor preparation.

In one preferred embodiment of the invention, at least one electrical resistance element preferably integrated on the semiconductor chip is connected to a processing device, which element consists of a material whose electrical resistance value is dependent upon the concentration of hydrogen gas; while the processing device will be configured in such a way that it analyzes a sensor signal from the resistance element for the detection of hydrogen gas. For this, the resistance element consists preferentially of a palladium-nickel alloy, whose specific electrical resistance varies in proportion to the concentration of hydrogen gas surrounding the resistance element. The resistance element is preferably in the form of a thin coating. It can be configured as a Gate-Electrode in the channel domain of a Field Effect Transistor (FET). The resistance element makes it possible to measure the concentration of hydrogen gas in the environment from approximately 0.5% to 100%. The processing device compares and analyzes the sensor signals from the SGFET, the Lundström-FET, and from the resistance element with one another, and thus it creates, from signals coming from three different kinds of hydrogen gas detecting sensors, one signal that measures hydrogen concentration.

Preferably the semiconductor chip will be provided with an electrical heating element. This would allow for the Lundström-FET to be heated in order to accelerate the diffusion of the gas to be detected into the second gas-sensitive coating, and thereby reduce the reaction time of the Lundström-FET's sensor signal to a change in gas concentration.

This heating can also be used to heat the resistance element.

It would be advantageous for at least one grooved depression to be made in the substrate, preferably on the backside of its gas-sensitive coating, which is so located relative to the heating element, that it will reduce the conduction of heat in a lateral direction. The groove can be formed as a ring or a window surrounding the heating device, or the heated area around the semiconductor chip. It is however also conceivable, that the groove would be shallow, and if need be, extend to the entire area of the substrate. When the semiconductor chip is prepared, first at least one Lundström-FET, at least one SGFE, and the processing device are placed upon the substrate; then a part of the substrate can be removed from the backside, using state-of-the-art methods, for example an etching process. In the region of the groove, the thickness of the substrate can be less than 70 µm and preferably less than 50 µm. Thanks to this groove, the semiconductor chip will have a low heat conduction in a lateral direction, and moreover, the groove will reduce the semiconductor chip's heat capacity.

In an advantageous embodiment of the invention, a temperature sensor, connected to the processing device, is integrated into the semiconductor chip, while the processing device is so configured that the gas detection occurs as a function of the temperature sensor's signal. As a result, it is in particular possible to compensate for the temperature dependence of the Source-Drain current of the field effect transistors, which is particularly advantageous when at least one gas sensor consists of a MOSFET.

In a preferred embodiment of the invention, the processing device would be configured in such a way that it would generate a differential signal and/or a sum signal from the sensor signals for both kinds of gas sensors, while the gas detection would result depending upon the differential- and/or sum signal. Because these two kinds of gas sensors have a differential cross-sensitivity vis a vis the target gas, it will be possible to use the differential signal to identify components of the signal which are caused by gases other than the target gas.

The processing device can be configured in such a way, that in detecting the gas, it will respond to the polarity and/or the quantity of the differential signal. From the polarity in particular, measurement signals or sections of measurement signals can be determined, which are induced by gases that bring about changes in sensor signal output in both kinds of sensors, which are oriented in opposite directions to each other.

It is particularly advantageous if the processing device is configured in such a way that it will produce a Quotient signal from the signals received from the two kinds of gas sensors, so that the detection of the gas depends upon the Quotient signal. The differential signal can then be compared to at least one given value or range of values, in order to detect the presence of a gas corresponding to a given value or range of values indicating cross-sensitivity. For detecting such a gas, the signals of the gas sensor which is characterized by cross-sensitivity can be ignored, or taken into consideration only in a weakened form, and the measurement of concentration of the relevant gas is performed primarily or exclusively by the other kind of gas sensor.

In a preferred embodiment of the invention, the device can be switched, with the help of a switching device, from fully operational to powersaving, where in the powersaving mode, the heating, and if necessary, the Lundström-FET are switched off; and where the processing device is configured in such a way that in the powersaving mode, it preferentially processes only the sensor signal from the SGFET for the detection of gas. With a leak-detection device for the hydrogen fuel line of a motor vehicle, the switching between fully operational and powersaving modes can be set up as a function of the motor vehicle's operational status. In this process, the system would be switched to fully operational when the fuel cells are switched on, in order to achieve the most precise leak detection, while the powersaving mode would be activated when the fuel cells are switched off, in order to spare the motor vehicle's battery.

In some cases it would be possible to design the switching device in such a way that it would switch from full operational to powersaving if the measured gas concentration exceeds a given standard value, so that the switching device if need be would likewise switch from powersaving to fully operational, if the gas concentration measured were to drop below the given standard value. In this case, the assumption is that the SGFET can measure a higher gas concentration than the Lundström-FET. The aforesaid standard value is preferably chosen in such a way that to some extent it will match the concentrations of the gases to be detected, which can be measured with the Lundström-FET when they are at maximum levels. In this way, whenever there are high concentrations of gas, mistaken readings due to the limits of the measurement range of the Lundström-FET, can be avoided and the energy demands of the device will be reduced.

It would be advantageous for the processing device to stand connected in a controlling relationship to the switch, in such a way that the powersaving mode would be switched over to the fully operational, if the SGFET sensor signal should be of a cross-section typical for the presence of the gas; and, if necessary return to the powersaving mode when such a sensor signal is no longer detected. When the SGFET is in the powersaving mode and detects a sensor signal which might have been caused by the gas to be detected, then the heating element, and if need be, the Lundström-FET are turned on, and then with the help of both kinds of sensor signals, a more precise measurement of the gas concentration can be made. If the suspicion of the presence of a prohibited high concentration of gas is confirmed in the process, an alarm will be sounded and/or the fuel line can be blocked. Thus, in spite of a reduced energy consumption, the device enables a reliable and precise detection of gas, in particular hydrogen gas.

The previously cited objective can also be solved by a device of the above-cited kind, where the Lundström-FET is located upon the substrate of a semiconductor chip of a first Drain and a first Source, between which a first channel domain is to be found, which is provided with a coating for detecting a second gas different from the first gas which is to be detected by the Lundström-FET, which reacts with a change in its output when there is a change in concentration of the target gas, and is capacitatively coupled across an air gap to a second channel domain; where the processing device is configured in such a way that for gas detection it analyzes the sensor signals relating to the presence of a gas mixture containing at least a first and a second gas, from both kinds of gas sensors.

These two gases might be such as those released by a fire; thus the device can be used to detect fires. Here it is also possible that a number of spatially separated semiconductor chips, each consisting of at least one Lundström-FET and one SGFET, will be connected to a central processing device. This can be connected to a fire alarm.

BRIEF DESCRIPTION OF THE DRAWINGS

One example of an embodiment of the invention is given below, and explained in more detail by means of a diagram. The following diagrams are shown.

DETAILED DESCRIPTION OF THE PREFERRED EMBODIMENTS

Figure 1:
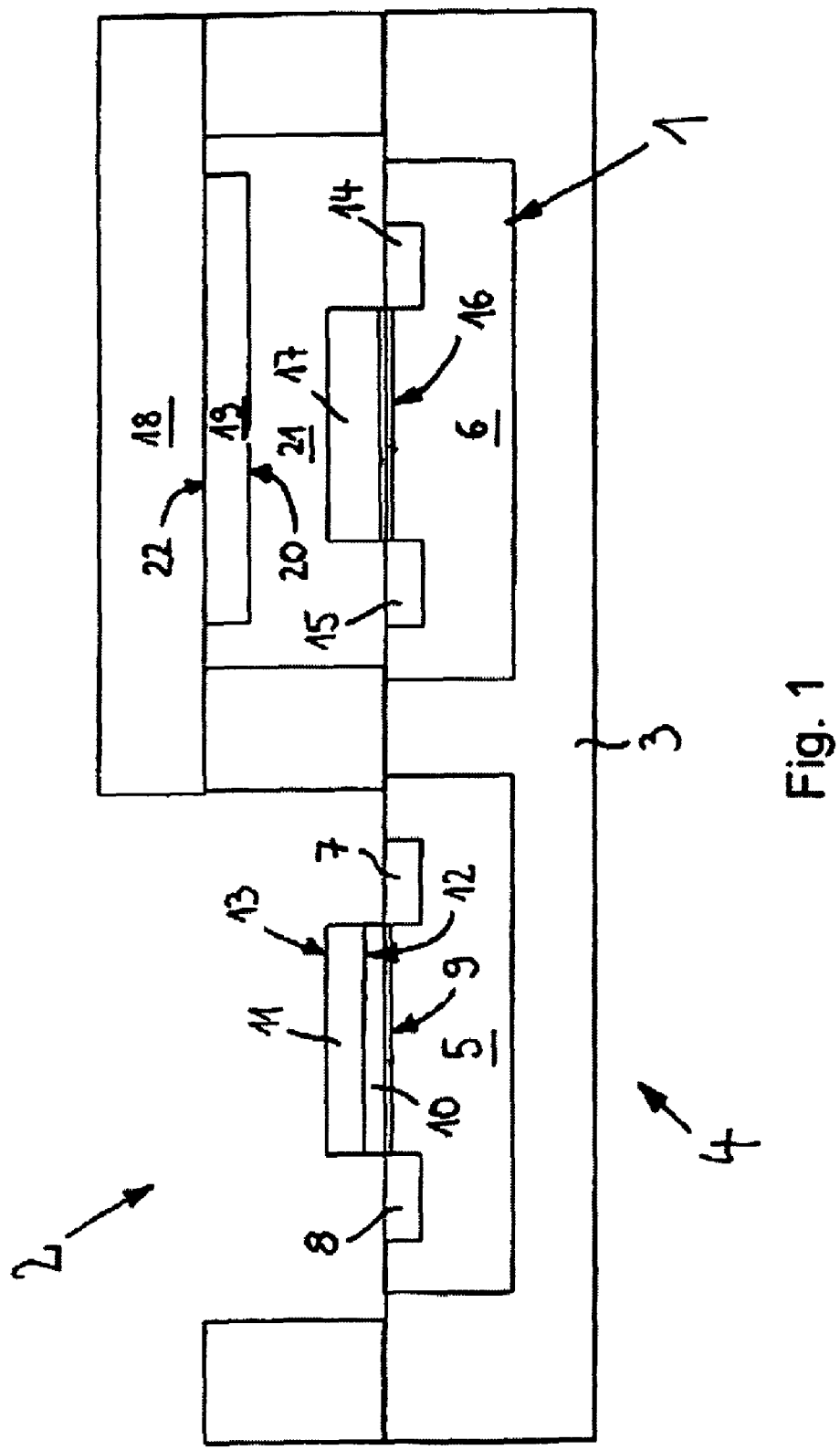
FIG. 1 A cross-section of a semi-conductor chip, where a Lundström-FET and an SGFET have been integrated to function as a hydrogen sensor, FIG. 2 A graphic presentation of the sensor signals of the SGFET and of the Lundström-FET, as a function of the hydrogen gas concentration, where the abscissa gives the Time, t, in hours and the ordinate to the left gives the changes in the output $\Delta\Phi$ in eV, and on the right, the concentration C of the hydrogen gas in ppm, FIG. 3 An illustration similar to FIG. 2, where however, instead of the concentration of hydrogen gas on the ordinate, the concentration of ammonia gas is given, and FIG. 4 An illustration similar to FIG. 2, where however, instead of the hydrogen gas concentration on the ordinate, the CH4 gas concentration is given.

A device for detecting a gas, namely hydrogen, for example in a motor vehicle which uses hydrogen as a fuel, has two kinds of sensors, namely an SGFET 1 and a Lundström-FET 2. The SGFET 1 and the Lundström-FET 2 are connected to a processing device which is not illustrated in detail in the drawing, which is configured in such a way, that it allows for the processing of sensor signals from both kinds of gas sensors, regarding the concentration of the hydrogen gas present in the neighborhood of the gas sensors.

In FIG. 1, it can be seen that the SGFET 1 and the Lundström-FET 2 are integrated on a substrate 3 in a semiconductor chip designated in its entirety by 4. It can be seen clearly that hollow zones are to be found in the surface of Substrate 3, which can be filled with charge carriers; these zones are called wells 5,6.

The left half of FIG. 1 shows a first well, 5, in which a first Drain 7 and a first Source 8, which are dedicated to the Lundström-FET 2, are located, and which are configured through areas which have the second type of charge carrier. Between the first Drain 7 and the first Source 8, a channel domain 9 is configured, which has been coated with a dielectric coating 10, and upon that, a first gas-sensitive coating 11, which consists of palladium and/or a palladium alloy.

The neighboring region 12 of the dielectric coating 10 of the first gas-sensitive coating 11, is capacitatively coupled between the dielectric coating 10 to the first channel domain 9. The first gas-sensitive coating 11 is electrically connected with the reference voltage junction. Hydrogen can be absorbed by an exposed surface 13 of the first gas-sensitive coating 11, and it can be diffused through coating 11 to reach the boundary surface 12.

In the lateral direction, besides the first well 5, there is a second well 6 to be found in the surface of the substrate 3, in which a second Drain 14 and a second Source 15 have been placed for the SGFET. Between the second Drain 14 and the second Source 15, a channel domain 16 is configured, which is covered with a thin insulating coating and upon that, a Gate Electrode 17.

On the side of the second channel domain 16 oriented away from the substrate 3, there is a second gas sensitive coating 19 oriented to the channel domain 16 on a bridge-like suspended gate 18 spanning the channel domain 16. The second gas-sensitive coating 19 consists of palladium, platinum and/or an alloy that contains at least one of these metals, and reacts in response to a change in the concentration of hydrogen with a change in its output.

The gas-sensitive coating 19 is capacitatively coupled with its flat surface 20, dedicated to the second channel domain 16, to the second channel domain 16 across an air gap 21 open to the immediate environment. On the back side 22 facing away from surface 20, a gas-sensitive coating 19 is connected via a conducting path not presented in more detail in the drawing, to a reference voltage junction, which has a defined voltage.

The Source-Drain zone of the SGFET is connected to a first sensor signal input; and the Source-Drain zone of the Lundström-FET 2 to a second sensor signal input of the processing device. In the processing device, the sensor signals from the two different kinds of gas sensors are first calibrated with the help of characteristic values placed into the memory, in order to smooth out any eventual initial tolerances, specifically the geometric dimensions of the gas sensors. After being calibrated in this way, the sensor signals are compared to one another and to characteristic values in the memory, and based on the results of this comparison, an alarm signal might be generated at the output port of the processing device, which would indicate the presence of hydrogen gas in the environment of the gas sensors.

Figure 2:
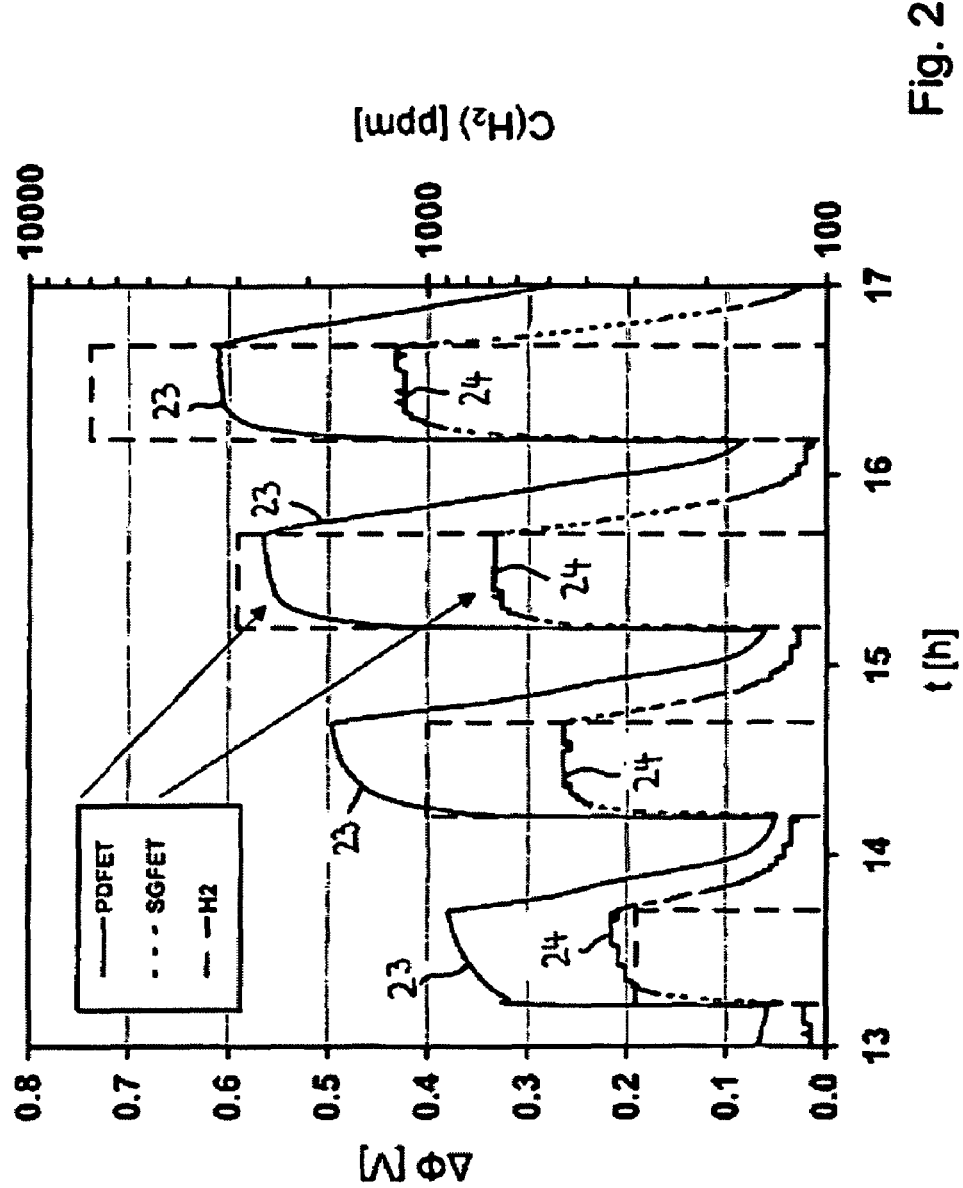

FIG. 2 shows that when the gas sensors make contact with a hydrogen gas, the sensor signal 23 of the Lundström-FET 2 is greater in magnitude than the sensor signal 24 of the SGFET 1. Here the Quotient of sensor signal 23 of the Lundström-FET and the sensor signal 24 of SGFET 1 is approximately 1:1.4. Moreover it can be seen that the sensor signals of both kinds of gas sensors have a similar response time. In FIG. 2 the dotted line shows the concentration of hydrogen gas. It is clear that over time the concentration of the hydrogen gas exhibits a number of right-angled pulses, which are separated form each other by pulse pauses, in which the hydrogen gas concentration is approximately zero. During the pulse pauses, each of the sensor signals 23, 24 from the two kinds of gas sensors diminishes, where the rate of the decrease diminishes in each case from the beginning of the relevant pulse pause to the end of the pulse pause.

Figure 3:
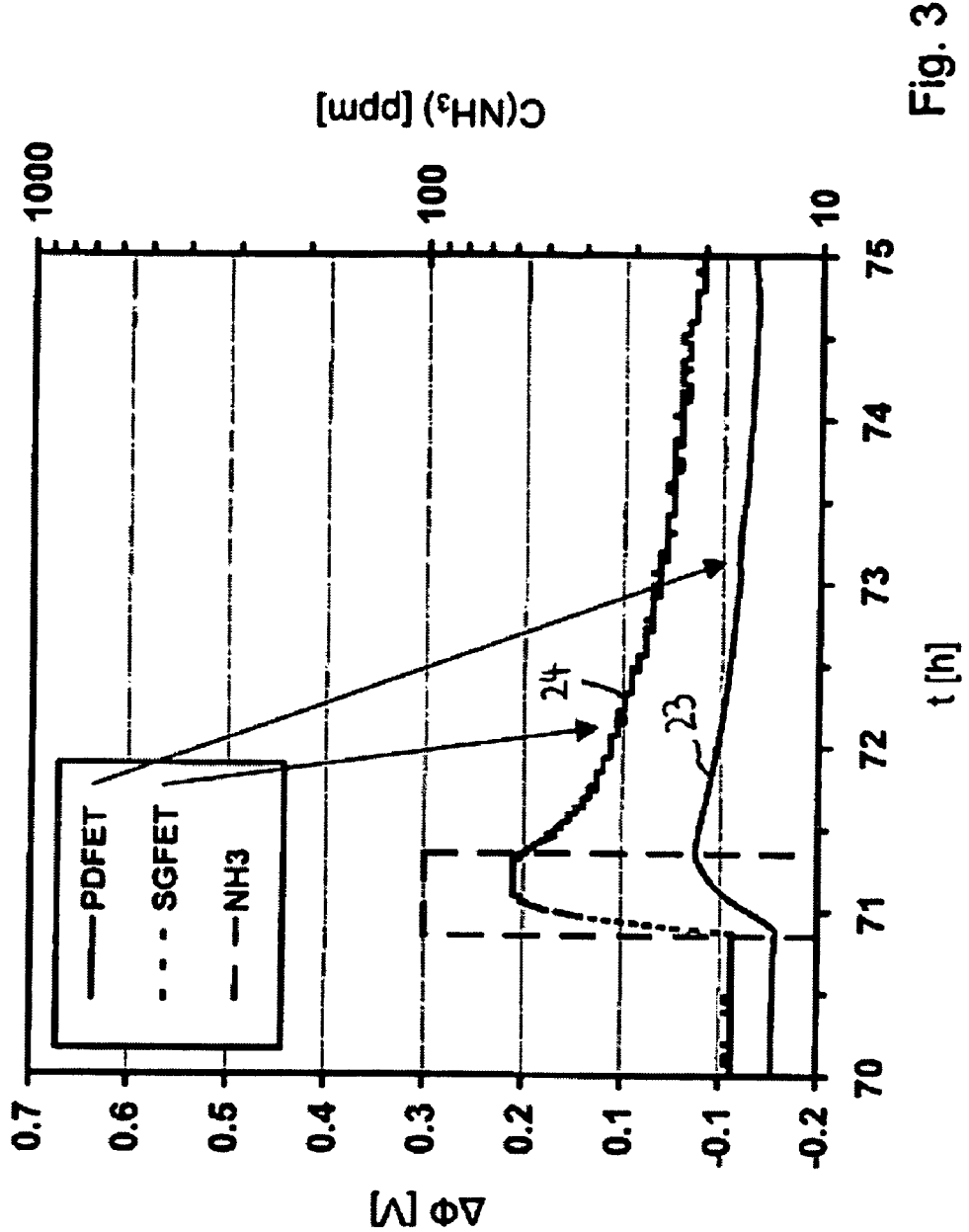

FIG. 3 shows the evolution over time of the gas sensor signal, when it is brought into contact with ammonia gas. It is clear that the sensor signal 23 of the Lundström-FET is smaller than the sensor signal 24 of the SGFET 1. The Quotient from the sensor signal 23 of the Lundström-FET 2 and the sensor signal 24 of the SGFET 1 now lies approximately between 2:1 and 3.3:1. Thus it is now possible to determine, as a function of the quotient of the sensor signals 23, 24, whether or not the gas sensors have come into contact with hydrogen or with another gas.

Figure 4:
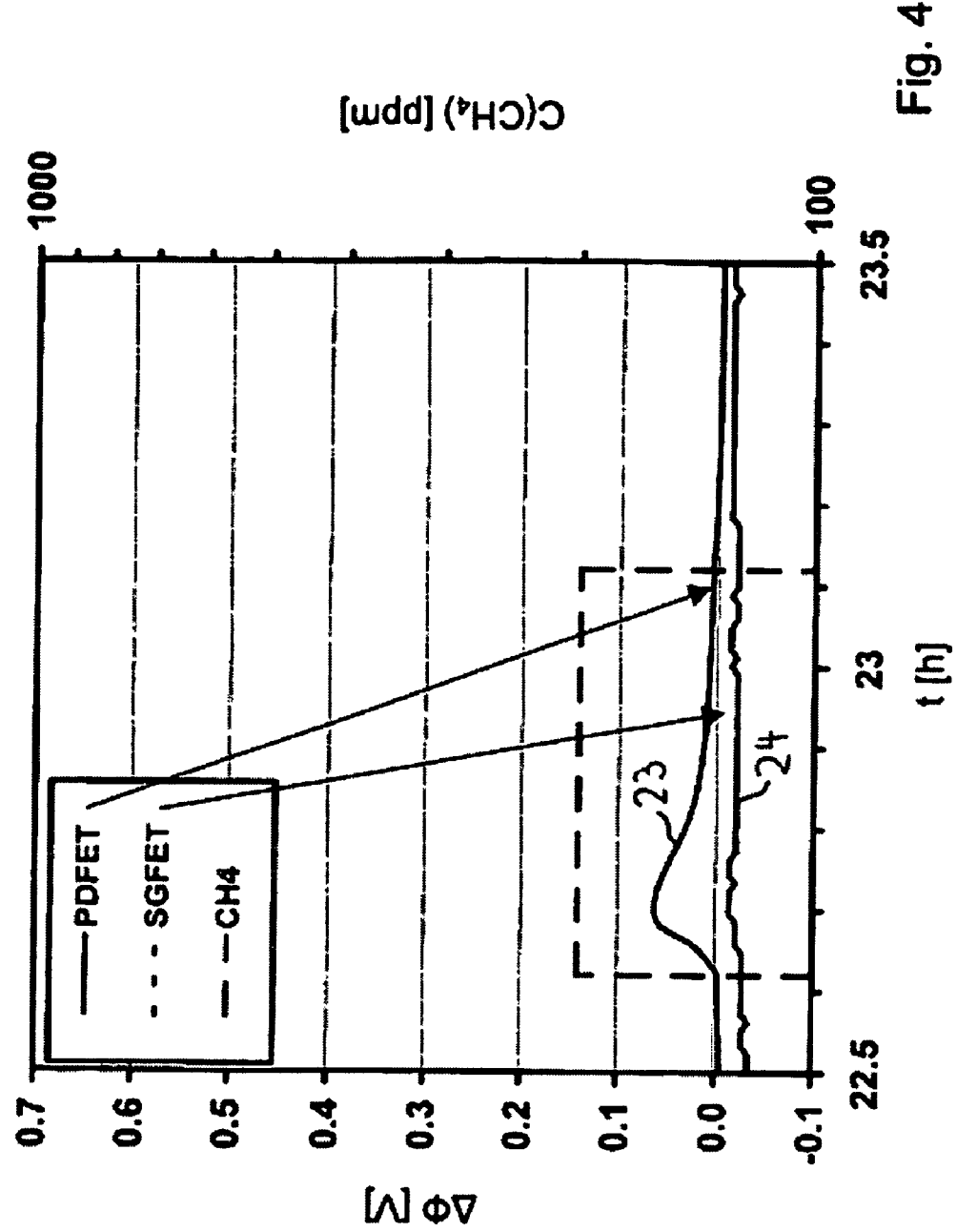

FIG. 4 shows the evolution of the gas sensor signal when the sensor comes in contact with methane, namely CH4. Here it can be seen that the CH4 essentially only changes the sensor signal 23 of the Lundström-FET 2, while the sensor signal 24 of the SGFET 1 shows practically no reaction. Moreover, it can be seen that the sensor signal 23 of the Lundström-FET 2 at first shows a constant CH4 concentration within a given time frame, then rises to a maximum value, and then falls to a value which is greater than the value which the sensor signal showed before the Lundström-FET 2 came into contact with the CH4 gas. This example makes it possible to conclude on the basis of sensor signals 23, 24 of the gas sensors, that these are not in contact with hydrogen.

The device for the gas detection thus consists at least of a first gas sensor consisting of an SGFET 1, and at least a second gas sensor consisting of an Lundström-FET 2. The gas sensors are connected to a processing device which is configured in such a way that it can process sensor signals 23, 24 of both kinds of gas detection sensors.

The invention claimed is:

1. A device for detecting a gas or a gas mixture, which has at least one Lundström-FET gas sensor, characterized in that it consists of, besides the Lundström-FET, at least one other gas sensor in the form of a Suspended Gate Field Effect Transistor (SGFET), and that at least one Lundström-FET and at least one SGFET are connected to a processing device, which is configured in such a way that it can analyze the sensor signals of both kinds of gas sensors in order to detect gases or gas mixtures.

2. A device according to claim 1, characterized in that the Lundström-FET on a substrate of a semiconductor chip has a first Drain and a first Source, between which there is a first channel domain, which has been covered with a first gas-sensitive coating that reacts by changing its output when there are changes in the concentration of the gas to be detected, and is capacitatively coupled across a dielectric coating to the first channel domain; that the SGFET has upon the substrate next to the Lundström-FET a second Drain and a second Source, between which there is a second channel domain, to which a gas-sensitive coating mounted on a Suspended Gate is dedicated, which responds with an output change when there is a change in the concentration of the gas to be detected, and/or a gas different from the gas to be detected, where the SGFET shows a sensitivity, reacts and is capacitatively coupled across an air gap to a second channel domain.

3. A device according to claim 1, characterized in that the relevant gases are hydrogen gas, ammonia or nitrous oxide; or that the gas mixture contains hydrogen gas, ammonia or nitrous oxide.

4. A device according to claim 1, characterized in that at least the second Drain, the second Source, the second channel domain and the Gate Electrode of at least one SGFET, at least one Lundström-FET and if need be, the processing device are integrated into the same semiconductor chip.

5. A device according to claim 1, characterized in that the first gas-sensitive coating consists of palladium and/or a palladium alloy, and the second gas-sensitive coating consists of palladium and/or platinum and/or an alloy containing at least one of these metals.

6. A device according to claim 1, characterized in that the Suspended Gate is laterally extended across the Lundström-FET, and preferably covers it completely.

7. A device according to claim 1, characterized in that there is one electrical resistance element integrated in the semiconductor chip connected to the processing device, which element consists of a substance whose electrical resistance is a function of the concentration of hydrogen; and that the processing device is configured in such a way that it analyzes a sensor signal of the resistance element to detect hydrogen gas.

8. A device according to claim 1, characterized in that an electrical heating element is integrated in the semiconductor chip.

9. A device according to claim 1, characterized in that the substrate preferably will have on the backside oriented away from the gas-sensitive coatings at least one groove, which is oriented to the heating element in such a way that it reduces the lateral conduction of the heat from the heating element.

10. A device according to claim 1, characterized in that the semiconductor chip has integrated into it a temperature sensor connected to a processing device, and that the processing device is so configured, that the gas detection is a function of the temperature sensor signal.

11. A device according to claim 1, characterized in that the processing device is so configured, that it generates a differential signal and/or a sum signal from the sensor signals of both kinds of gas sensors, and that the gas detection results as a function of the differential and/or sum signal.

12. A device according to claim 1, characterized in that the processing device is configured in such a way, that the detection of gas is a function of the polarity and/or the magnitude of the differential signal.

13. A device according to claim 1, characterized in that the processing device is so configured that it generates a Quotient signal from the sensor signals of both kinds of gas sensors, and that the detection of gas occurs as a function of the Quotient signal.

14. A device according to claim 1, characterized in that with the help of a switching device, the heating element and the Lundström-FET can be switched back and forth between a fully operational condition and a powersaving condition, and that the processing device is so configured that during a powersaving condition, it can preferentially detect only the sensor signal of the SGFET.

15. A device according to claim 1, characterized in that the switching device is so configured that it can switch from fully operational to the powersaving mode when the measured concentration of gas exceeds a given standard value, and that likewise the switching device can switch back from the powersaving mode to the fully operational mode, when the measured concentration of gas declines below the given standard value.

16. A device according to claim 1, characterized in that the processing device is connected with the switching device in such a way, that in the powersaving mode, when a section of a sensor signal typical for the presence of a gas to be detected occurs in the sensor signal of the SGFET, the switching device switches to the fully operational mode, and as the case may be, if such a sensor signal is no longer detected, once again switches back to the powersaving mode.

17. A method for powering a device according to claim 1 in a machine fueled by gas and used for the production of electrical and/or mechanical energy, for example a fuel cell and/or a motor vehicle, wherein the energy producing machine is put into one mode of operation to produce electrical and/or mechanical energy, and is then changed over to a second mode in which the energy production is switched off, and wherein the device is switched between the fully operational or the powersaving mode as a function of the operating mode of the energy production machine.

18. A device for detecting a gas or a gas mixture, which has at least one Lundström-FET gas sensor, wherein the Lundström-FET is located upon a substrate of a semiconductor chip and has a first Drain and a first Source, between which a first channel domain is to be found, which is provided with a gas-sensitive first coating, which reacts by changing its output when there is a change in the concentration of a first gas, and is capacitatively coupled across a dielectric coating to the first channel domain, characterized in that the device consists of at least one Suspended Gate Field Effect Transistor (SG-FET), which has adjacent to it on the substrate, besides a Lundström-FET, a second Drain and a second Source, between which a second channel domain is to be found, where a second sensor is located, which detects gases different from those detected by the Lundström-FET, which has a second sensitive coating, which changes its output when there is a change in the target gas concentration, and is capacitatively coupled across an air gap to a second channel domain, and that the processing device is so configured that it analyzes the signals from both kinds of sensors to detect a gas mixture made up of at least two gases.

* * * * *